United States Patent [19]

Kelsen

[11] 4,047,527
[45] Sept. 13, 1977

[54] ORAL SYRINGE

[76] Inventor: Arthur F. Kelsen, 11701 Foster Road, Los Alamitos, Calif. 90720

[21] Appl. No.: 634,023

[22] Filed: Nov. 21, 1975

[51] Int. Cl.² .............................................. A61M 3/00
[52] U.S. Cl. ........................................ 128/229; 128/66
[58] Field of Search .................... 128/229, 66, 173.1, 128/210, 211, 274; 239/310, 312, 315, 316, 427, 414; 137/625.29, 625.34, 604, 607; 251/100, 321

[56] References Cited

U.S. PATENT DOCUMENTS

| 1,654,745 | 1/1928 | Miller | 128/229 |
|---|---|---|---|
| 1,950,680 | 3/1934 | Johns | 128/229 |
| 2,272,381 | 2/1942 | Marvin | 128/229 |
| 2,849,256 | 8/1958 | Kowal | 128/229 X |
| 2,938,517 | 5/1960 | Friend | 128/66 |
| 3,054,402 | 9/1962 | Franwick et al. | 128/229 |
| 3,401,691 | 9/1968 | Beu | 128/229 X |
| 3,477,687 | 11/1969 | Doutt | 251/100 |
| 3,500,824 | 3/1970 | Gilbert | 128/66 |
| Re. 26,288 | 10/1967 | Clark, Jr. | 251/100 X |

Primary Examiner—J. Reed Fisher
Attorney, Agent, or Firm—Roger A. Marrs

[57] ABSTRACT

An oral syringe is disclosed herein for introducing a pressurized stream of water to the user for irrigating the gums and teeth for the purpose of massage and cleansing. A manual valve mechanism is interposed in a passageway provided in the handle of the syringe for stopping the conduction of the pressurized stream therethrough and for diverting the stream into a mixing chamber for combining the stream with another substance such as mouthwash or for conducting the stream to a discharge nozzle without mixing. The valve mechanism includes a depression action as well as a rotary action to achieve the control functions.

1 Claim, 8 Drawing Figures

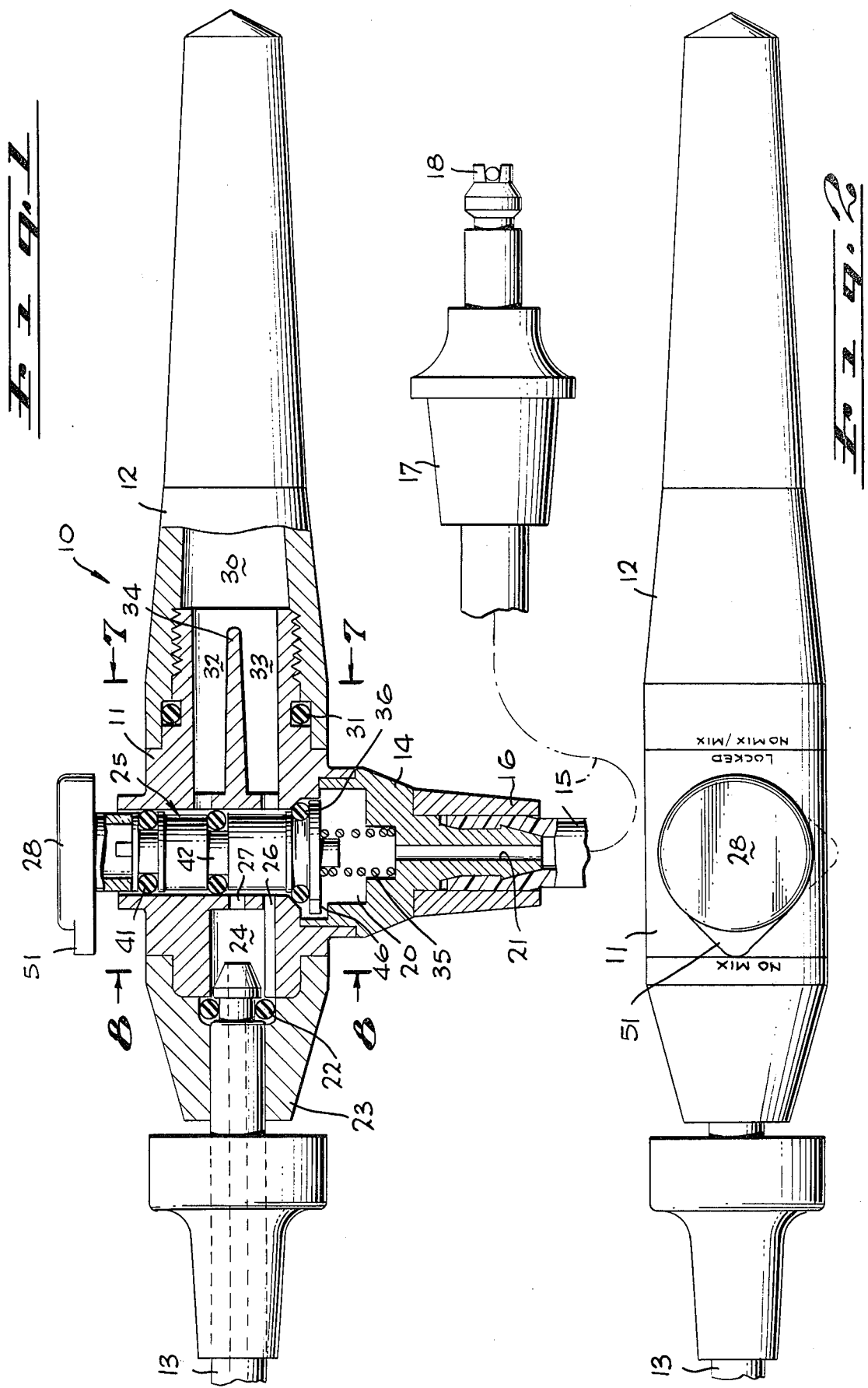

ORAL SYRINGE

BACKGROUND OF THE INVENTION

1. Field of the Invention

This invention relates to oral hydrotherapeutic devices for the promotion of oral hygiene and, more particularly, to an improved oral syringe having a unique control valve for effecting a clear pressurized stream discharge or a discharge of stream water mixed with an augmenting substance and which further includes a stop control.

2. Description of the Prior Art

Medical science has demonstrated in the past that a thorough cleansing of teeth and gums greatly assists in protecting and promoting human health and comfort. Where trapped debris and microorganisms (and their metabolic products) are removed from the cervical surfaces of the teeth next to gum margins, calculus accumulation or tartar is prevented since the inorganic salts necessary for producing such accumulation will deposit and calcify only when the organic matrix of this deposit is present. When this removal process is accomplished by a fluid stream, the inherent cyclic pressure and relaxation results in increased circulation in the underlying tissues thereby promoting healthier gums.

For these reasons, mechanical devices for cleaning teeth and massaging gums have been heretofore widely proposed, and probably the instrument most commonly used today for such purposes is the toothbrush. There are, however, several serious disadvantages inherent in the utilization of toothbrushes for gum massage and teeth cleaning. For one thing, patience and practice are required to develop the necessary skill needed, since careless brush placement and vigorous scrubbing can puncture, lacerate and/or seriously bruise the facial gingiva. As a result, it is quite common to punctate lesions to appear as red pinpoint dots corresponding to the tips of the toothbrush bristles or as linear scratches where the bristle tips were drawn over the gums with excessive pressure. Consequently, it is not unusual for an overzealous toothbrush used with a new stiff-textured toothbrush to brush too long in one or two areas and thereby remove the surface epithelium, producing a raw, painful bruise.

While oral hydrotherapeutic syringes are known to be of great assistance and value for loosening debris adhering to and/or trapped between teeth, their utilization has heretofore been severly curtailed as a result of their complexity, costliness and the fact that they have been difficult to use and control. Perhaps more importantly, for such devices to achieve general acceptance, they must be able to be attached to, and detached from, common fluid sources such as home water faucets with a minimum of time and effort.

While numerous devices of this general purpose have been proposed in the past, they have generally fallen short of the accomplishment of the desired ends in various aspects. Many, for example, have been designed to become permanently affixed to the fluid source which, in the case of a home water faucet, necessarily interferes with the normal operation and utilization thereof.

Another aspect in which the prior art has fallen short is the narrow scope or purpose for which such devices have heretofore been proposed such as in the device described in U.S. Pat. Nos. 3,225,759 and 3,500,824. This scope has been expanded by the present invention which, in part, permits the user thereof to meter desired amounts of mouthwash into his or her mouth under pressure so that portions of the gums (or gingiva) between the teeth can be rinsed, disinfected and the debris flushed out from between crevices.

By selectively utilizing a mouthwash in conjunction with the cleaning and massaging action of the syringe, the soft tissues within the mouth are soothed, resulting in accelerated healing of sore spots. The removability feature of the mouthwash container also permits the user to utilize a variety of washes which are particularly suited to his or her needs such as mouthwashes containing various germicidal, astringent, deodorant, buffering or therapeutic properties.

SUMMARY OF THE INVENTION

The problems and difficulties encountered with conventional dental syringe devices for the promotion of oral hygiene are obviated by the present invention which provides, in one embodiment thereof, an elongated body having a control portion and a handle portion detachably connected thereto which is provided with a mixing chamber. A control valve mechanism is carried in the control portion and includes means for selectively intercommunicating the control portion with the mixing chamber of the handle and for interconnecting a pressurized water inlet with the mixing chamber or with a discharge nozzle. A feature of the invention resides in the fact that the control valve incorporates a valve mechanism which is rectilinear in movement when depressed for some control functions while rotary in action for other functions.

Therefore, it is among the primary objects of the present invention to provide a novel oral syringe for introducing a therapeutic mouthwash into the mouth under pressure and in conjunction with a pressurized main carrier stream of fluid for cleansing the teeth and massaging the gums.

Another object of the present invention is to provide a novel hand operated dental syringe capable of storing mouthwash and mixing the mouthwash with a main carrier stream via a control valve operable by depression and rotary action for performing various functions.

Still another object of the present invention is to provide a novel hand held oral syringe having a control mechanism which is positive in nature and which is fool proof with respect to the control by the operator for performing a variety of functions.

Still a further object of the present invention is to provide a novel control mechanism for a hand held dental syringe which will operably connect a plurality of conduits or fluid passageways in a selected manner for permitting the issuance of a main carrier stream under pressure, mixing mouthwash with the main carrier stream or for inhibiting discharge of the main carrier stream from the device.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is a longitudinal cross sectional view of the novel hand held dental syringe of the present invention illustrating the control mechanism in position for inhibiting the main carrier stream flow;

FIG. 2 is a top plan view of the hand held dental syringe shown in FIG. 1 illustrating the rotary position of the control mechanism;

DESCRIPTION OF THE PREFERRED EMBODIMENT

Figure 3:
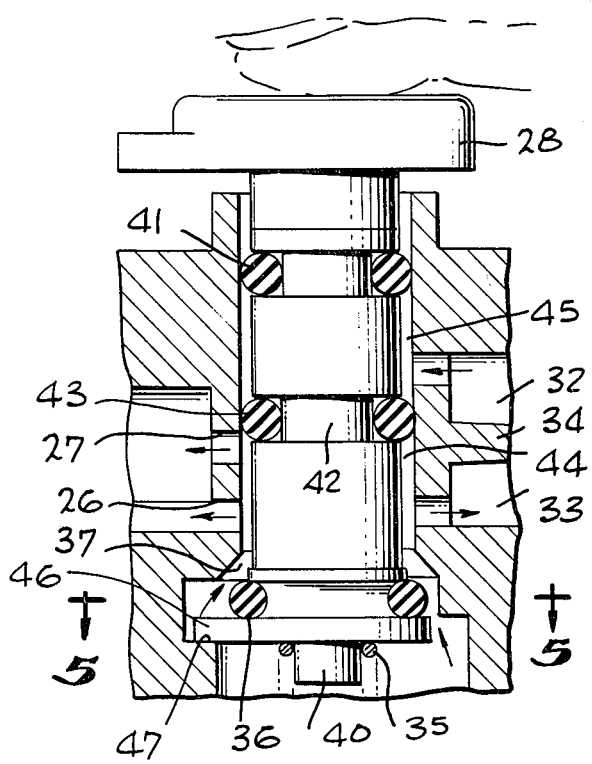
FIG. 3 is a enlarged transverse cross sectional view of the control valve mechanism illustrating the mechanism in position for discharging the pressurized main carrier stream.

Referring to FIG. 1, the novel hand held oral syringe of the present invention is indicated in the general direction of arrow 10 which includes an elongated handle comprising a central body portion 11, a handle portion 12 which is threadably attached to the central portion 11 and a nozzle discharge portion 13 detachably connected to the opposite side of the central portion from the handle portion. Downwardly depending from the central portion 11 is an attachment portion 14 to which a hose 15 is secured via an interference fit with a ferrule 16. Hose 15 is attached at its other end to a suitable means or releasable plug 17 having an end 18 suitable for insertion into a socket carried on an aerator valve assembly (not shown) detachably connected to a conventional sink faucet. Such an attachment device is disclosed in U.S. Pat. No. 3,500,824.

The oral syringe 10 receives a pressurized supply of fluid, such as water, constituting the main carrier stream from the water faucet. The water faucet is coupled to a suitable pressurized source of supply of water and the faucet may be located in a sink or basin installed in a bathroom, restroom, comfort station or the like. The oral syringe 10 is detachably connected to the aerator valve assembly by means of the flexible supply conduit or hose 15 which is in fluid communication with an internal chamber 20 via passageway 21 provided in attachment portion 14. The main body portion 11 detachably couples with nozzle 13 which outwardly projects from one end thereof and is detachably coupled thereto by means of a sealing ring 22 carried on a ferrule 23. The nozzle 13 is in fluid communication with a outlet chamber 24 which is selectively connected in fluid communication by a valve mechanism 25 with inlet chamber 20. Fluid communication is achieved through a pair of output ports 26 and 27 controllable by means of the valve mechanism 25.

The handle 12 is detachably connected to the other end of the main body portion 11 which is employed for convenience of operation and handling. Preferably, the handle 12 is cylindrically configured so as to be readily hand-held across the palm of a user's hand so that the forefingers of the hand embrace the body while the thumb is in a suitable position for operating a pushbutton arrangement 28 adapted to position the valve mechanism 25, to be described later. It is noted that the handle 12 includes an interior cavity 30 which is employed for holding a quantity of mouthwashes particularly suited to the user's needs. An O-ring 31 seals the detachable connection between the handle 12 and the main body portion 11 and it is further noted that the body portion includes an input port or passageway 32 and an outward port 33. The latter mentioned port or passageways are substantially separated by a partition 34; however, it is understood that the passageways are in fluid communications with each other and the mixing chamber 30. Also, it is to be noted that the passageways or ports 32 and 33 are also in fluid communication at selective times depending upon the valve mechanism 25 with the input chamber 20.

Referring now in detail to the valve mechanism 25, it can be seen that the pushbutton 28 is fixedly secured to the mechanism so that the mechanism will depress when the pushbutton is pressed down by the thumb of the user and the mechanism will rotate when the user manually turns the pushbutton or thumb cap 28. The valve mechanism is normally shown in its "off" position in FIG. 1 because of the bias of the spring 35. It is noted that the bias of spring 35 urges the valve mechanism 25 upwardly in the central housing or portion 11 until a seal 36 forcibly closes against annular shoulder 37 formed on the body 11 and defining the upper limit of chamber 20. When seal 36 is urged against the shoulder 37, the flow of fluid from chamber 20 into either port 26 or 32 is prohibited. Therefore, the control mechanism as seen in FIG. 1 is in its normal non-use condition whether the plug 17 is attached to a pressurized water faucet or not.

It is to be further noted that the valve mechanism 25 constitutes an elongated spindle or element terminating in one end with a guide 40 acting as a centering means for the spring 35 and providing a bearing surface against which the spring is forcibly in contact. The mechanism further includes the sealing ring 36 located near the centering element 40 and a sealing ring 41 carried on the member adjacent to the pushbutton cap 28 so as to prevent the fluid from leaking between the main body portion 11 and the valve. Midway between the opposite ends of the valve stem or member 25, there is provided a groove 42 which holds an annular seal 43 so that annular chambers exist between the opposing wall surface of the bore in body portion 11 and the exterior surface of the valve mechanism or stem 25. The first of the pair of chambers may be identified by numeral 44 and the second annular chamber is identified by numeral 45. The first and second annular chambers are selectively aligned with the respective input and output ports for intercommunicating the chambers upon the depression and/or rotation of the valve stem.

Referring now in detail to FIG. 3, the position of the control mechanism 25 is such that the pressurized main carrier stream of fluid is introduced from the chamber 20 to the output port 26 and 27 via the annular chamber 44. When the user's finger depresses the valve stem against the expanding pressure of spring 35, the stem moves downward toward chamber 20 until a lip 46 engages with a shoulder 47. No further depression can take place as a positive stop is produced. However, the pressurized main carrier stream can progress past the extreme end of stem 25 and flow around seal 36 as noted by the adjacent arrows thereto. The flow of the carrier stream as it passes annular seal 36 travels into the annular chamber 44 past stop shoulder 37 and into fluid communication with output ports 26 and 27 for discharge through the nozzle. It is to be noted that fluid communication exists between annular chamber 44 and passageway 32 and 33 so that the main carrier stream is present. However, annular seal 43 prevents any discharge or flow from the port 33 since the seal 43 is blocking fluid communication with respect to the output port. Therefore, there is no flow of the main carrier stream through ports 32 and 33 or through annular chamber 45.

Figure 4:
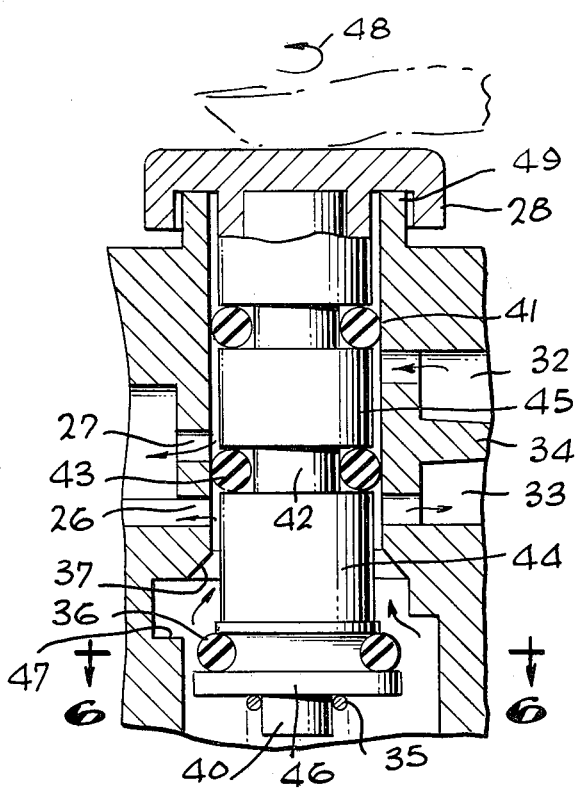
FIG. 4 is a view similar to the view of FIG. 3 illustrating the control mechanism in position for mixing the main carrier stream with the mouthwash ingredient for combined discharge through the nozzle.

However, when the valve mechanism 25, including the stem, is rotated in a counterclockwise direction as shown by arrow 48 in FIG. 4, the lip 46 disengages with shoulder 47 and the stem is permitted to depress spring 35 even further under the pressure of the user's finger. The valve stem will depress until the underside of the cap 28 engages with the shoulder stop 49 carried on the main portion 11. However, it is now noted that the chamber 45 is placed in fluid communication with output port 27. It is to be noted that the annular chamber 44 is still maintained in fluid communication with the output port 26. Therefore, any mouthwash or other ingredient which is carried in the cavity 30 is mixed with the main carrier stream and is introduced to the discharge nozzle via chamber 45 and outlet port 27. Simultaneously, a portion of the main carrier stream of fluid is introduced through the outlet port 26 via annular chamber 44 where it is combined with the mixed fluid from port 27 and discharged through the nozzle as a stream.

Figure 5:
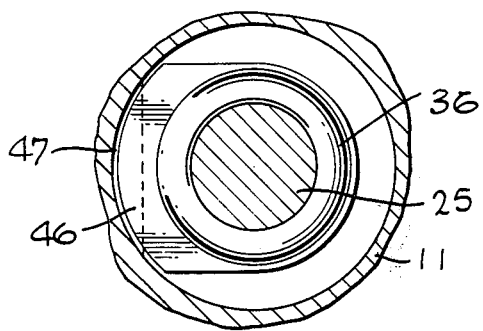
FIG. 5 is a cross sectional view taken in the direction of arrow 5—5 of FIG. 3.
Figure 6:
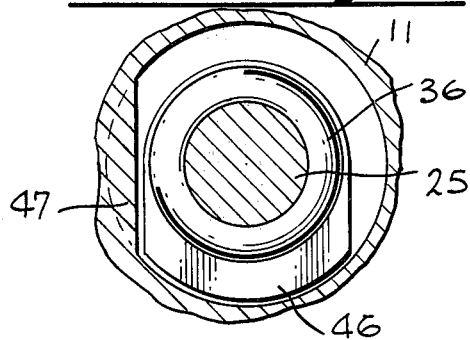
FIG. 6 is a cross sectional view of the control mechanism taken in the direction of arrow 6—6 of FIG. 4.
Figure 7:
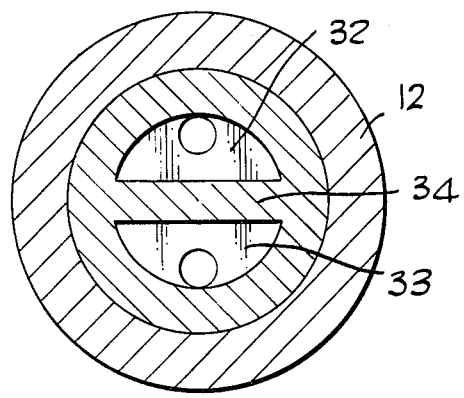
FIG. 7 is a cross sectional view of the handle portion of the dental syringe taken in the direction of arrow 7—7 of FIG. 1.
Figure 8:
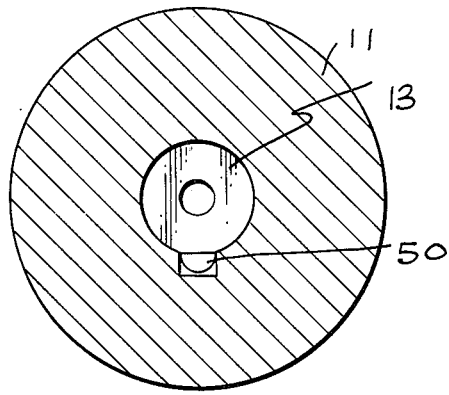
FIG. 8 is a cross sectional view taken in the direction of arrow 8—8 of FIG. 1.

In FIGS. 5 and 6, the location of stem or valve mechanism 25 is illustrated between the two positions shown in FIGS. 3 and 4 respectively. In FIG. 7, the ports 32 and 33 are illustrated and their partial separation by means of partition 34. In FIG. 8, the combined discharge of fluid from ports 26 and 27 are through the discharge nozzle 13. A snap-lock arrangement indicated by element 50 is employed for snap-locking the nozzle into place with main body portion 11.

Rotation of the cap 28 is further illustrated in FIG. 2 and it is to be noted that markings or proper indicia may be placed on the housing or handle respectively so as to be properly placed in registry or indexed with a pointer 51 carried on the cap 28. For example, the words "no mix" can be placed so that when the pointer or marker 51 is adjacent thereto, the valve mechanism or stem 25 is in the position shown in FIG. 1 so that no flow is permitted to issue from the nozzle. When it is desired to have the main carrier stream discharge from the nozzle without mixing, the button can be depressed so that the valve mechanism or stem 25 assumes the position as shown in FIG. 3. When it is desired to mix the contents of th chamber 30 with the main carrier stream, the pushbutton 28 may be rotated approximately 90° to the position shown in broken lines in FIG. 2 whereupon the mechanism can be depressed even further to assume the position shown in FIG. 4 so that the mixed main stream discharge can take place from the nozzle.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An oral hydrotherapeutic syringe for delivering a fluid carrier stream to the teeth for effecting the cleaning thereof and for massaging the gums, the combination comprising:
a syringe having a central body portion;
a handle detachably connected to said body portion and provided with a mixing chamber for storing a quantity of mouthwash;
a nozzle detachably connected to said body portion for discharging said main carrier stream;
an attachment portion including an inlet chamber coupled to a source of pressurized fluid constituting said main carrier stream;
a control mechanism operably carried on said central body portion between said nozzle, said mixing chamber and said inlet chamber for selectively conducting said main carrier stream therebetween;
said control mechanism including a valve means responsive to manual depression for interconnecting said inlet chamber to said nozzle for discharge of said main carrier stream and responsive to rotation thereof in cooperation with axial rectilinear displacement of said valve means to interconnect said mixing chamber with said nozzle simultaneously with said interconnected inlet chamber for a combined discharge of said mouthwash with said main carrier stream;
said valve means includes an elongated spindle mounted for rectilinear and rotary movement on said central body portion;
at least three seals carried on said spindle is fixed spaced apart relationship so as to define a pair of annular fluid conducting chambers between adjacent seals;
a first chamber of said pair operable in response to a first depression of said valve means to interconnect said inlet chamber with said nozzle and said mixing chamber;
a second chamber of said pair operable in response to simultaneous rotation and a second further depression of said valve means to interconnect said mixing chamber with said nozzle simultaneously with said interconnection between said inlet chamber and said nozzle via said first chamber;
stop means limiting said rectilinear movement of said valve means;
said stop means includes a projection carried on one end of said spindle releasably engageable with a lip provided on said central body portion so as to prevent depression of said valve means beyond said intercommunication of said inlet chamber with said mixing chamber and said nozzle;
said stop means further includes interference of a selected one of said seals with said central body portion to arrest movement of said valve means so as to close communication between said inlet chamber with said mixing chamber and said nozzle;
spring biasing means yieldably urging said selected seal into engagement with said central body portion; and
indicia displayed on said central body portion for mixing and no-mixing; and
said valve means having a pushbutton carried on said spindle incorporating a pointer operable with said indicia to visually display the rotational position of said valve means.

* * * * *